United States Patent [19]

Karjalainen et al.

[11] Patent Number: 5,098,923
[45] Date of Patent: Mar. 24, 1992

[54] AROMATASE INHIBITING 4(5)-IMIDAZOLES

[75] Inventors: Arto J. Karjalainen, Oulu; Lauri V. M. Kangas, Raisio; Kauko O. A. Kurkela, Turku; Reino O. Pelkonen, Oulu, all of Finland

[73] Assignee: Farmos-Yhtyma Oy, Turku, Finland

[21] Appl. No.: 588,873

[22] Filed: Sep. 27, 1990

Related U.S. Application Data

[63] Continuation-in-part of Ser. No. 254,054, Oct. 6, 1988, abandoned.

[30] Foreign Application Priority Data

Oct. 9, 1987 [GB] United Kingdom ............. 8723715

[51] Int. Cl.⁵ .................. A61K 31/415; C07D 233/64
[52] U.S. Cl. ................... 514/396; 514/400; 548/335; 548/342
[58] Field of Search ............ 548/342, 335, 341; 514/396, 400

[56] References Cited

FOREIGN PATENT DOCUMENTS

| | | |
|---|---|---|
| 0034473 | 8/1981 | European Pat. Off. |
| 0034474 | 8/1981 | European Pat. Off. |
| 0058047 | 8/1982 | European Pat. Off. |
| 0064820 | 11/1982 | European Pat. Off. |
| 0072615 | 2/1983 | European Pat. Off. |
| 0165779 | 12/1985 | European Pat. Off. |
| 0194984 | 9/1986 | European Pat. Off. |
| 2096987 | 10/1982 | United Kingdom |

Primary Examiner—Mary C. Lee
Assistant Examiner—Lenora Miltenberger
Attorney, Agent, or Firm—Armstrong, Nikaido, Marmelstein, Kubovcik & Murray

[57] ABSTRACT

Imidazole derivatives of the formula:

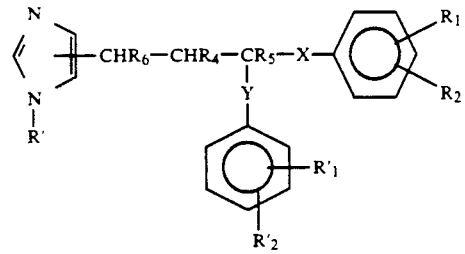

wherein $R_1$, $R_2$, $R'_1$ and $R'_2$ which can be the same or different, are H, $CH_3$, $C_2H_5$, $OCH_3$, OH, $CH_2OH$, $NH_2$ or halogen; R' if H or

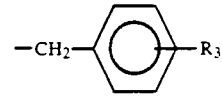

where $R_3$ is H, $CH_3$, or halogen; $R_4$ is H and $R_5$ is H or OH and $R_6$ is H or OH or one of $R_5$ and $R_6$ is H and the other, together with $R_4$, forms a bond and X and Y, which can be the same or different, are a bond, a straight $C_{1-2}$-alkyl or the corresponding alkenyl, and pharmaceutically acceptable salts thereof exhibit valuable pharmacological properties, especially aromatase inhibiting effects and are useful in the treatment of estrogen dependent diseases, e.g. breast cancer. Antimycotic and antifungal properties have also been found.

17 Claims, No Drawings

AROMATASE INHIBITING 4(5)-IMIDAZOLES

The present application is a continuation-in-part of application Ser. No. 07/254,054 (Karjalainen et al) filed Oct. 6, 1988 now abandoned.

The present invention relates to substituted imidazole derivatives and their non-toxic, pharmaceutically acceptable acid addition salts, and their preparation, to pharmaceutical compositions containing the same and to their use.

The imidazole derivatives of the present invention have the general formula:

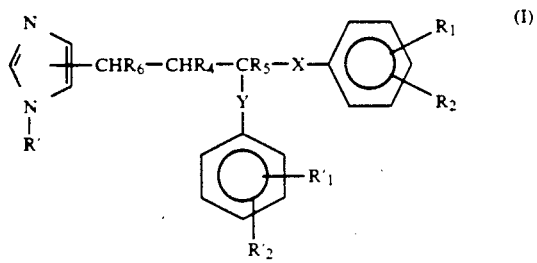

wherein $R_1$, $R_2$, $R'_1$ and $R'_2$, which can be the same or different, are H, $CH_3$, $C_2H_5$, $OCH_3$, OH, $CH_2OH$, $NH_2$ or halogen; R' is H or

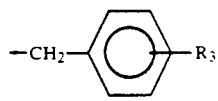

where $R_3$ is H, $CH_3$ or halogen; $R_4$ is H and $R_5$ is H or OH and $R_6$ is H or OH or one of $R_5$ and $R_6$ is H and the other forms, together with $R_4$, a bond, and X and Y, which can be the same or different, are a bond, a straight $C_{1-2}$-alkyl or the corresponding alkenyl.

The non-toxic pharmaceutically acceptable acid addition salts of these compounds are also within the scope of the invention.

The closest compound of the prior art to the compounds of the invention is 4-(2,2-diphenylethyl)-1H-imidazole. This compound was described in EP-194984 (Continental Pharma) as having selective $\alpha_2$-blocking properties. This compound was encompassed in the general formula of compounds of EP-A-165779 (Eli Lilly) disclosing compounds said to be aromatase inhibitors. There is a clear preference in EP-A-165779 for compounds in which the ethyl group is substituted with —$CONH_2$.

The compounds of the formula (I) form acid addition salts with both organic and inorganic acids. They can thus form many pharmaceutically usable acid addition salts, as, for instance, chlorides, bromides, sulfates, nitrates, phosphates, sulfonates, formates, tartrates, maleates, citrates, benzoates, salicylates, ascorbates and the like.

The invention includes within its scope pharmaceutical compositions comprising at least some of the compounds of formula (I) or a non-toxic, pharmaceutically acceptable salt thereof, and a compatible pharmaceutically acceptable carrier therefor.

The invention provides in particular a substituted imidazole of the formula:

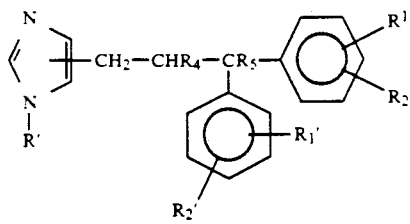

or a non-toxic pharmaceutically acceptable acid addition salt thereof wherein $R_1$, $R_2$, $R'_1$ and $R'_2$ which can be the same or different are H, $CH_3$, $C_2H_5$, $OCH_3$, OH, $CH_2OH$, $NH_2$ or halogen; R' is H or

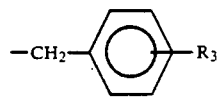

where $R_3$ is H, $CH_3$ or halogen; $R_4$ is H and $R_5$ is H or $R_4$ and $R_5$ together form a bond. The substituted imidazole may be one in which $R_4$ and $R_5$ are both H. When $R_4$ and $R_5$ are both H, preferably at least one of $R_1$, $R_2$, $R'_1$ and $R'_2$ is not H and one or more of the substituents $R_1$, $R_2$, $R'_1$ and $R'_2$ are in the 3, 4, 5, 3', 4' or 5' positions of the phenyl groups, for example, compounds wherein $R_2$ and $R'_2$ both are H and $R_1$ and $R'_1$ are both not H and are both in the meta or para positions of the phenyl groups and compounds wherein $R_2$, $R'_2$ and $R'_1$ each are H and $R_1$ is not H and is in the para position of the phenyl group.

The substituted imidazole may be one in which $R_4$ and $R_5$ together form a bond. If so, then preferably $R_2$ and $R'_2$ are both H and $R_1$ and $R'_1$ are both not H and are both in the meta or para position of the phenyl groups.

The substituted imidazole may be one in which R' is H, or R' is

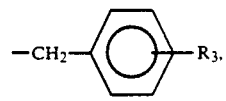

where $R_3$ is H, $CH_3$ or halogen. Preferably $R_3$ is H.

The invention provides, for example, the following specific compounds of formula (I):

4-(3,3-diphenyl-3-hydroxypropyl)-1H-imidazole
4-[3,3-bis(4-chlorophenyl)-3-hydroxypropyl]-1H-imidazole
4-[3,3-bis(2-methylphenyl)-3-hydroxypropyl]-1H-imidazole
4-[3,3-bis(3-methylphenyl)-3-hydroxypropyl]-1H-imidazole
4-(3,3-diphenylpropen-2-yl)-1H-imidazole
4-[3,3-bis(4-chlorophenyl)propen-2-yl]-1H-imidazole
4-[3,3-bis(2-methylphenyl)propen-2-yl]-1H-imidazole
4-[3,3-bis(3-methylphenyl)propen-2-yl]-1H-imidazole
4-(3,3-diphenylpropyl)-1H-imidazole
4-[3,3-bis(2-methylphenyl)propyl]-1H-imidazole
1-benzyl-5-[3,3-bis(4-chlorophenyl)-3-hydroxypropyl]-1H-imidazole
1-benzyl-5-[5-(2,6-dimethylphenyl)-3-hydroxy-3-(2,6-dimethylphenylethyl)pentyl]-1H-imidazole 1-benzyl-5-[3,3-bis(4-chlorophenyl)propen-2-yl]-1H-imidazole
4-[3-(4-chlorophenyl)-3-hydroxy-3-phenylpropyl]-1H-imidazole
1-benzyl-4-(3,3-diphenylpropyl)-1H-imidazole
1-benzyl-5-(3,3-diphenylpropyl)-1H-imidazole
4-[5-(2,6-dimethylphenyl)-3-(2,6-dimethylphenylethyl)pentyl]-1H-imidazole
4-[3,3-bis(3-methylphenyl)propyl]-1H-imidazole 1-(4-chlorobenzyl)-4-(3,3-diphenylpropyl)-1H-imidazole
1-(4-chlorobenzyl)-5-(3,3-diphenylpropyl)-1H-imidazole
4-[5-(2,6-dimethylphenyl)-3-hydroxy-3-(2,6-dimethylphenylethyl)pentyl]-1H-imidazole
4-[3,3-bis(3-fluorophenyl)propen-2-yl]-1H-imidazole
4-[3,3-bis(3-fluorophenyl)propyl]-1H-imidazole
4-[3,3-bis(3,5-dimethylphenyl)propyl]-1H-imidazole
1-benzyl-5-(3,3-diphenylpropen-2-yl)-1H-imidazole
1-benzyl-5-[3,3-bis(3,5-dimethylphenyl)-3-hydroxypropyl]-1H-imidazole
1-benzyl-5-[3,3-bis(3,5-dimethylphenyl)propen-2-yl]-1H-imidazole
1-benzyl-5-[3,3-bis(2-methoxyphenyl)propen-2-yl]-1H-imidazole
1-benzyl-5-[3,3-bis(3-methoxyphenyl)propen-2-yl]-1H-imidazole
1-benzyl-5-[3,3-bis(4-methoxyphenyl)propen-2-yl]-1H-imidazole
1-benzyl-5-[3,3-bis(2,3-dimethylphenyl)propen-2-yl]-1H-imidazole
1-benzyl-5-[3,3-bis(2-methylphenyl)propen-2-yl]-1H-imidazole
1-benzyl-5-[3,3-bis(3-methylphenyl)propen-2-yl]-1H-imidazole
1-benzyl-5-[3,3-bis(4-methylphenyl)propen-2-yl]-1H-imidazole
1-benzyl-5-[3,3-bis(3,5-dimethylphenyl)propyl]-1H-imidazole
1-benzyl-5-[3,3-bis(3-methoxyphenyl)propyl]-1H-imidazole
4-[3,3-bis(3,5-dimethylphenyl)propyl]-1H-imidazole
4-[3,3-bis(2,3-dimethylphenyl)propyl]-1H-imidazole
4-[3,3-bis(2-methoxyphenyl)propyl]-1H-imidazole
4-[3,3-bis(3-methoxyphenyl)propyl]-1H-imidazole
4-[3,3-bis(4-methoxyphenyl)propyl]-1H-imidazole
4-[3,3-bis(4-methylphenyl)propyl]-1H-imidazole
1-benzyl-5-(3,5-diphenylpentyl)-1H-imidazole
4-[3,3-bis(4-methoxyphenyl)propyl]-1H-imidazole
4-(3,4-diphenylbutyl)-1H-imidazole
4-[3-(4-methylphenyl)-3-phenylpropyl]-1H-imidazole
4-[3,3-bis(2-methoxyphenyl)propyl]-1H-imidazole
4-[3-(4-fluorophenyl)-3-phenylpropyl]-1H-imidazole
4-[3,3-bis(4-fluorophenyl)propyl]-1H-imidazole
1-benzyl-5-(3,3-diphenylpropen-1-yl)-1H-imidazole The compounds of the present invention have been found to inhibit selectively aromatase and are therefore valuable in the treatment of estrogen dependent diseases, e.g. breast cancer. Antimycotic and antifungal properties have also been found.

According to a feature of the invention, the compounds of formula I wherein the branches

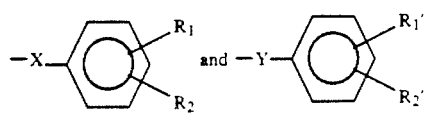

are identical are prepared by a successive sequence of reactions comprising a Grignard reaction of 4(5)-imidazole propionic acid alkyl ester (II) or its 1-benzyl derivative III with an appropriate aryl- or arylalkyl-magnesium halide IV following the loss of water and hydrogenation

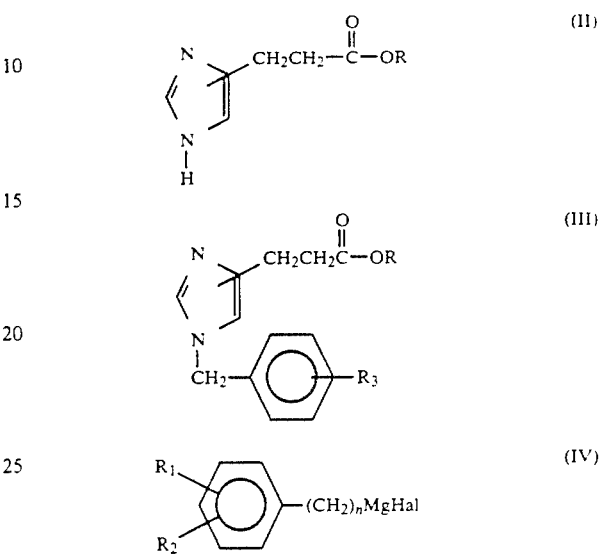

In the formulae (II) to (IV) R is alkyl, $R_3$ is H, $CH_3$ or halogen, n is 0 to 2 and $R_1$ and $R_2$, which can be the same or different, are H, $CH_3$, $C_2H_5$, $OCH_3$, OH, $CH_2OH$, $NH_2$ or Hal (Hal=halogen). The first reaction step, the Grignard-reaction, leads to the following compounds of formula (I):

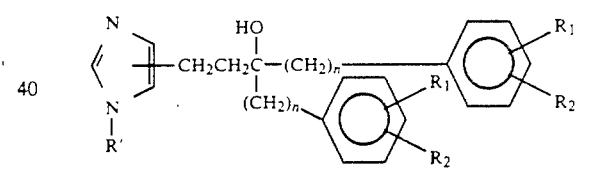

In this reaction the arylalkylmagnesium halide derivative can be, for example, an arylalkylmagnesiumbromide derivative, which is prepared by reacting the corresponding arylalkylbromide derivative with magnesium. Suitable solvents for the reaction include a variety of ethers, preferably tetrahydrofuran.

The arylalkylmagnesiumhalide derivative is prepared in the usual way by adding the arylalkylhalide derivative in a suitable solvent, e.g. tetrahydrofuran, dropwise onto magnesium turnings covered by tetrahydrofuran, at the boiling point of the reaction mixture. When the magnesium turnings have reacted, the mixture is cooled slightly and the 4(5)-imidazole propionic acid alkyl ester or its 1-benzylsubstituted derivative is added in solid form in small portions or dropwise in tetrahydrofuran.

After the addition, the reaction mixture is refluxed until all of the 4(5)-imidazole derivative has reacted. The reaction time varies between one and five hours.

Further according to the feature of the invention, the compounds of formula (I), wherein $R_4$ and $R_5$ both are hydrogen or together form a bond, are prepared by dehydration of the compounds of formula (I), where $R_5$ is OH, and by catalytic addition of hydrogen in the second step. Water is eliminated by usual methods, i.e. by heating with concentrated hydrochloric acid or by heating with dry potassium hydrogen sulfate. The unsaturated derivatives (V) (the compounds of formula (I) wherein $R_4$ and $R_5$ together form a bond) are isolated and after that hydrogenated. Alternatively they can be hydrogenated directly in an acid medium without previous isolation. The hydrogenation is conveniently carried out at room temperature with good stirring in alcohol, e.g. ethanol in the presence of a catalyst in a hydrogen atmosphere. Suitable catalysts are for example platinum oxide, palladium-on-carbon or Raney-nickel.

The reaction scheme for these steps can be illustrated as follows:

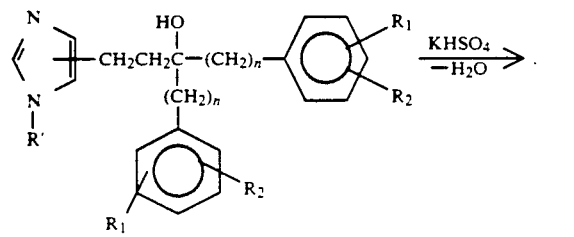

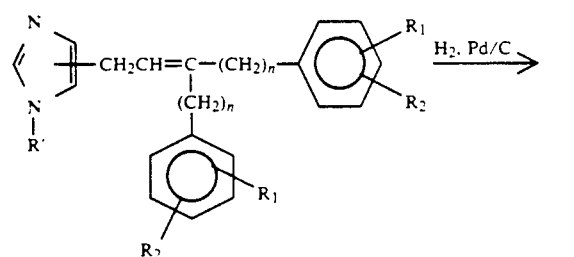

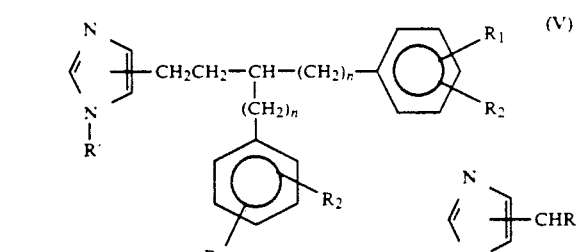

If R' is a substituted or unsubstituted benzyl, this group may be removed by hydrogenation as well. In this case the hydrogenation is performed in an acidic medium such as hydrochloric acid-ethanol mixture at elevated temperature.

The reaction scheme of this hydrogenation which leads to compounds of formula (I) wherein $R_4$ and $R_5$ both are hydrogen can be illustrated as follows:

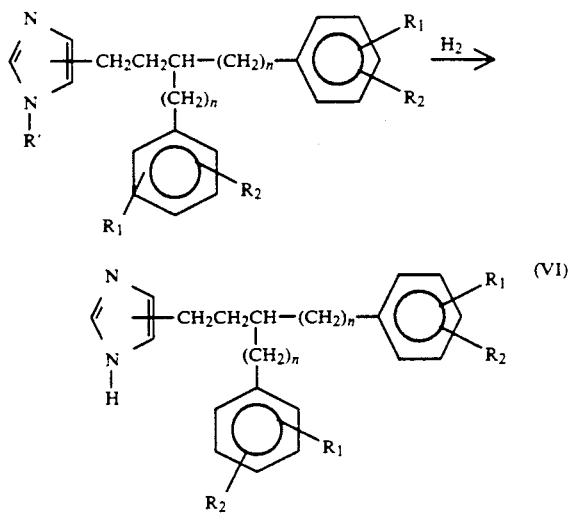

The compounds (VI) can also be prepared directly from the compounds (V) by hydrogenating both the double bond and the protecting benzyl group at the same time.

Another method for the preparation of compounds of formula (I) where R' is a benzyl is the benzylation of the corresponding compound where R' is hydrogen. The starting compound is first treated with a strong base such as sodium hydroxide in water or sodium hydride in an appropriate solvent, e.g. dimethyl formamide to give the alkali metal salt of the imidazole and then in the second step adding to this benzyl halide. The reaction scheme can be illustrated as follows:

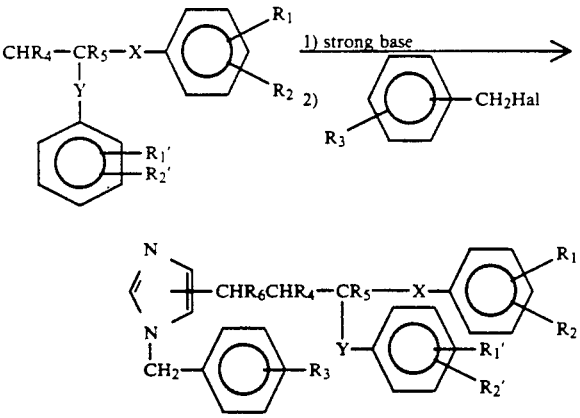

Yet another process for the preparations of compounds of formula (I) wherein the branches

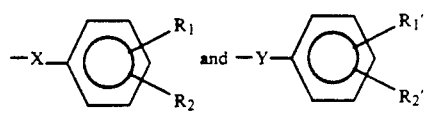

are different, comprises in the first stage a series of two successive Grignard reactions starting from 4(5)-imidazole propionic acid alkyl ester or from 1-benzyl-4(5)-imidazole propionic acid alkyl ester as previously. Now, however, the amount of the Grignard reagent is reduced as well as the reaction temperature, to stop the reaction at the ketone stage to give the 4(5 5)-imidazolylpropyl aryl or arylalkyl ketone (VII), which further is reacted with another Grignard reagent (VIII) to give a compound of formula (I) where R₅ is OH. The reactions are illustrated as follows:

catalyst, 4-imidazole propionic acid is formed. The subsequent treatment with alcohol, e.g. methanol, in the presence of dry hydrochloric acid leads to 4-imidazole propionic acid alkyl ester, which is used as starting material in the Grignard reaction:

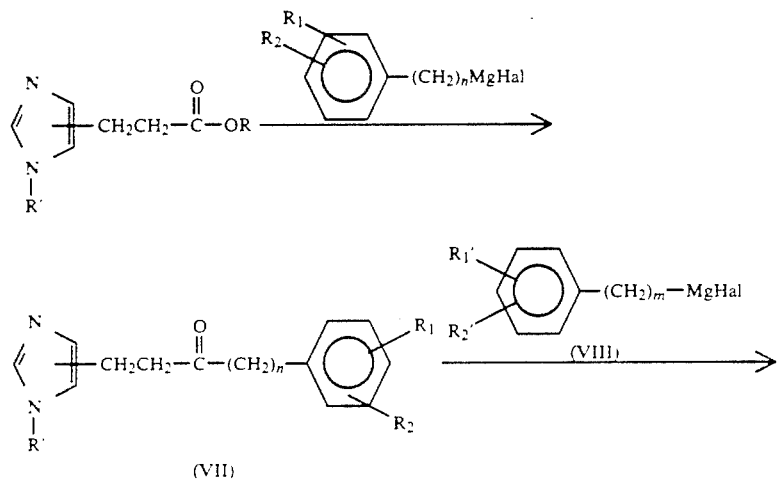

In the reaction scheme above m and n, which can be the same or different, are 0 to 2.

Choosing appropriate conditions for the dehydration of the compounds of formula (I) where R₅ is OH results in the corresponding compounds of formula (I) where one of the alkyl chains X or Y is transformed to the corresponding alkenyl chain.

In order to achieve a better control of the reactions above, as starting material may be used an amide of the 4(5)-imidazole propionic acid as well. Especially suitable in this respect is for example a piperidinyl amide of the formula

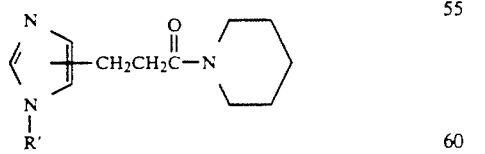

In the processes described above, the 4(5)-imidazole propionic acid esters (II) and (III) may be prepared for example starting from 1-benzyl-5-imidazole carbaldehyde and malonic acid, which are condensed together to form a 5-(1-benzylimidazole)acrylic acid. When this compound is hydrogenated under acidic conditions at elevated temperature (70°-80° C.) in the presence of a

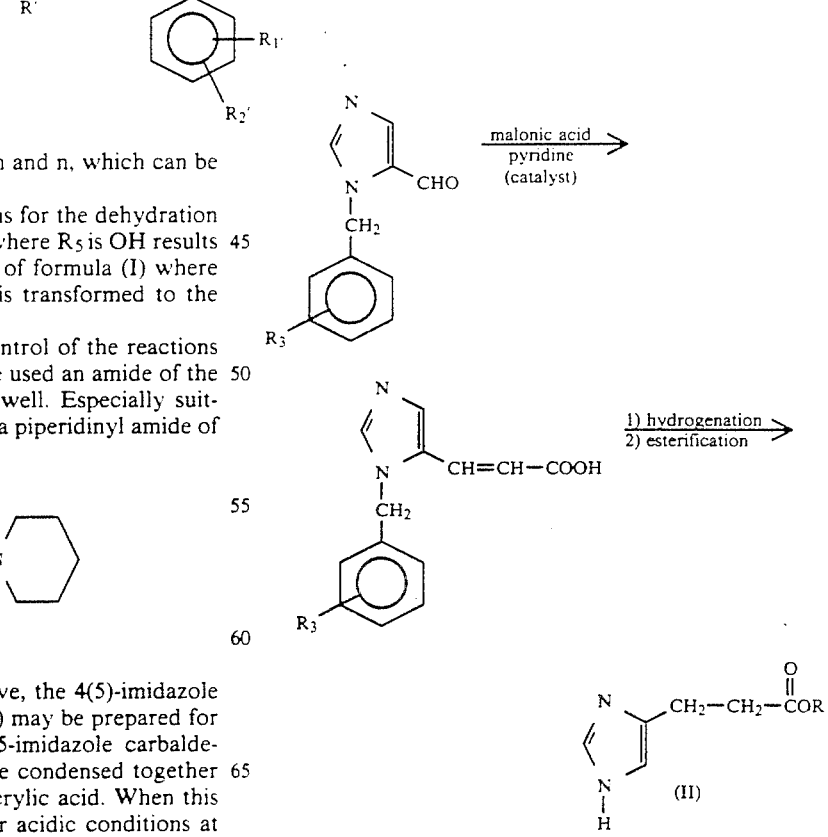

When 5-(1-benzylimidazole) acrylic acid (the benzyl group may be substituted or unsubstituted) is hydrogenated at room temperature in alcohol 1-benzyl-5-imidazole propionic acid is achieved. The following treatment with alcohol in the presence of dry hydrochloric acid at elevated temperature leads to another possible starting material for the Grignard reaction, namely 1-benzyl-5-imidazole propionic acid alkyl ester. The described reaction steps can be conducted in the opposite order as well. The reaction schemes are as follows:

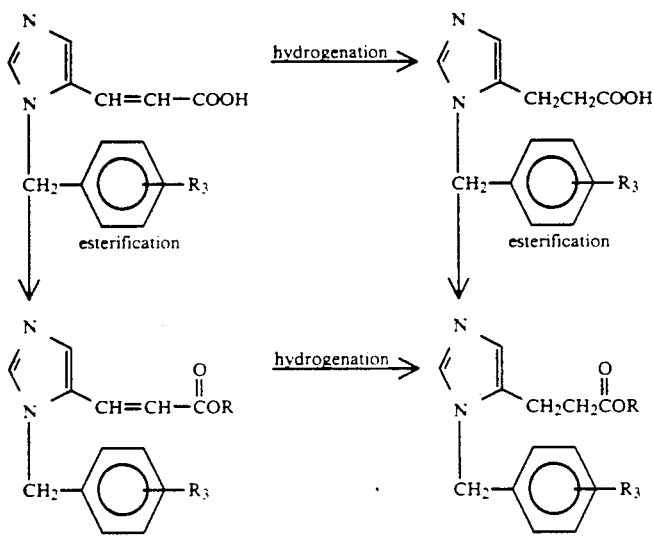

The compounds of formula (I) can be prepared by the Witting reaction and the Grignard reaction wherein the starting compound is an 4(5)-imidazole aldehyde (IX). In the formula (IX) R' is as defined before.

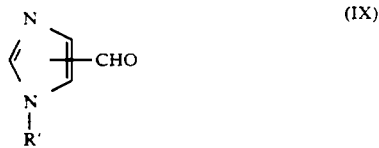

In the Witting reaction the first step is to prepare a phosphonium salt (X) from the corresponding halogenated hydrocarbon (XI) by reacting it with triphenylphosphine. The reaction scheme can be illustrated as follows:

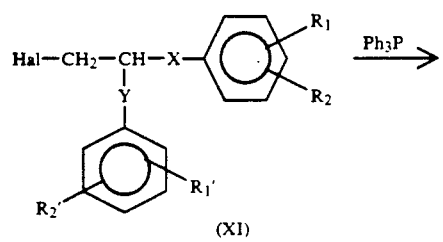

-continued

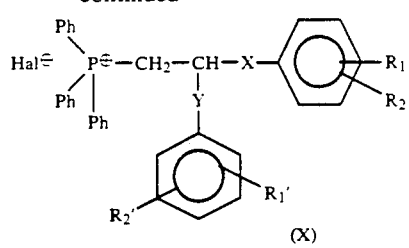

in which $R'_1$, $R'_2$, $R_1$, and $R_2$ are as hereinbefore defined.

In the second step of the Witting reaction the compound (X) is treated with a strong base to form a phosphorus ylide which is further allowed to react with the 4(5)-imidazole aldehyde (IX) to achieve the compounds of formula (I) wherein $R_4$ and $R_6$ together form a bond (XII). The strong base can be NaH or BuLi in a proper solvent such as dimethoxyethane, tetrahydrofuran or DMF. Further alkali metal alkoxides the corresponding alcohols as solvent and NaH in DMSO can be used as proton acceptors. The compounds (XII) are isolated and after that hydrogenated as has been described before to achieve the compounds of formula (I) wherein $R_4$ and $R_6$ both are hydrogen. The reaction scheme for these steps can be illustrated as follows:

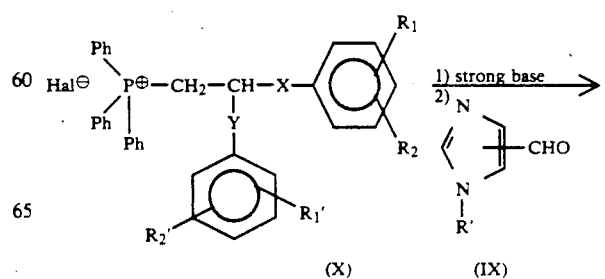

-continued

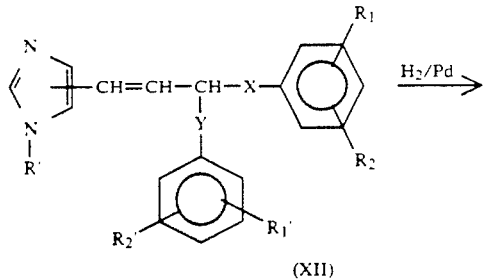

(XII)

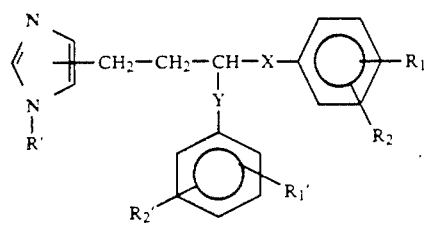

(XII)

The compounds of formula (I) can also be prepared by a modified Witting reaction, namely the Horner-Emmons or Wadsworth-Emmons reaction where the phosphonate (XIII) which is prepared from the halogenated hydrocarbon (XI) and a triester of phosphonic acid (e.g. (EtO)₃P) by the Arbuzow reaction reacts firstly with a base (e.g. NaH in DMSO or in dimethoxyethane) and then with the aldehyde (IX). The product (XII) formed is a compound of formula (I) where R₄ and R₆ together form a bond. The reaction scheme can be illustrated as follows:

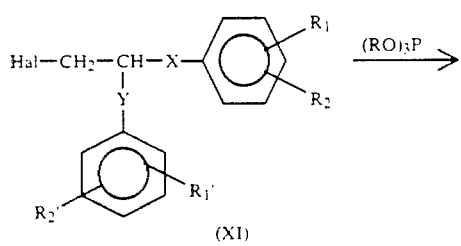

(XI)

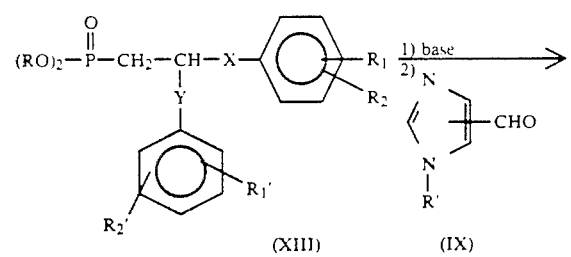

(XIII)   (IX)

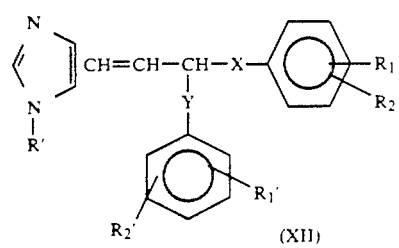

(XII)

In the formula (XIII) R is alkyl with 1–4 carbon atoms and R₁, R₂, R₁', R₂', X and Y are as defined before. The unsaturated compounds (XII) are further hydrogenated to form the compounds of formula (I) wherein R₄ and R₆ both are hydrogen.

Further method to prepare the compounds of formula (I) is the Grignard reaction in which the 4(5)-imidazole aldehyde (IX) is allowed to react with a Grignard reagent (XIV) to give a compound of formula (I) where R₆ is OH (XV). The Grignard reagent is prepared by reacting the corresponding halogenated hydrocarbon with magnesium turnings in the usual way. The compound (XV) is further dehydrated by heating with KHSO₄ or by refluxing in acidic alcohol to achieve the compounds of formula (I) where R₄ and R₆ together form a bond (XII). The unsaturated derivatives are then hydrogenated to form the compounds of formula (I) wherein R₄ and R₆ both are hydrogen. The reaction scheme for these steps can be illustrated as follows:

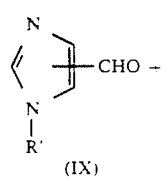

(IX)

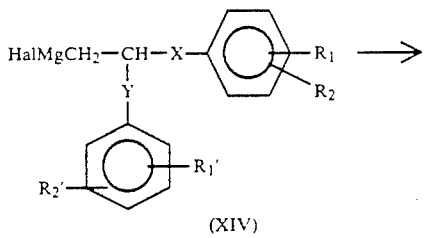

(XIV)

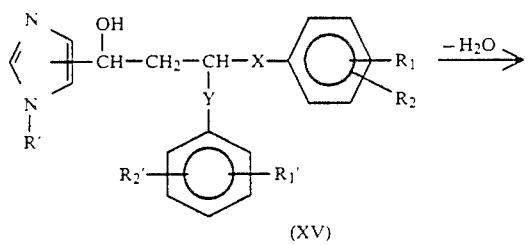

(XV)

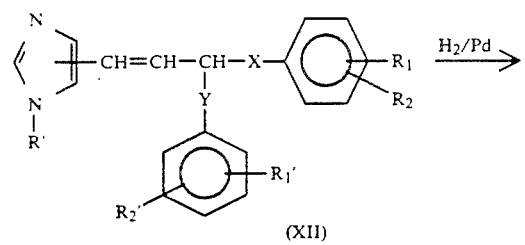

(XII)

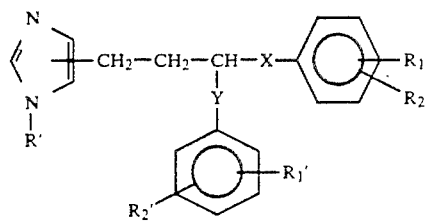

Further the compounds of formula (I) can be prepared by a Grignard reaction where the Grignard reagent (XVI) is prepared from a 4(5)-imidazolylalkyl-halogenide (XVII)

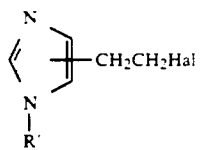
(XVII)

by allowing it to react firstly with magnesium and then with a suitable ketone (XVIII)

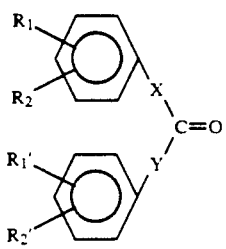
(XVIII)

The reaction scheme of this reaction which leads to compounds of formula (I) where $R_5$ is OH (XIX) can be illustrated as follows:

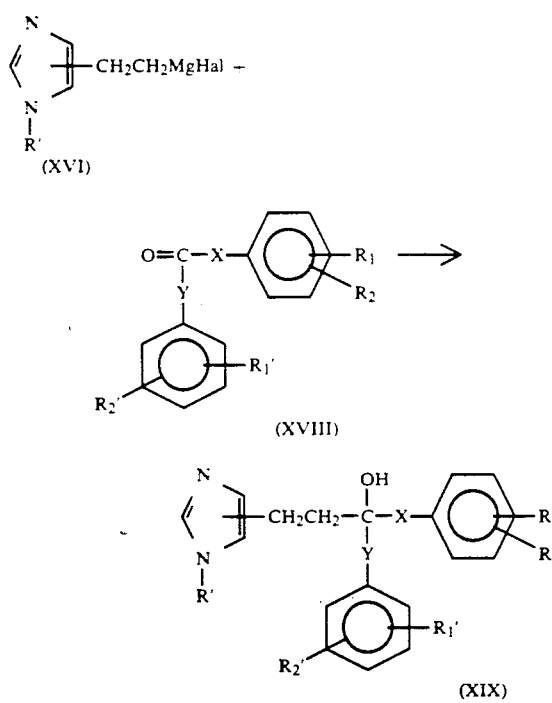

The compounds (XIX) can further be dehydrated and hydrogenated as described before to achieve the compounds of formula (I) wherein $R_4$ and $R_5$ both are hydrogen.

Administration of compounds of formula (I), their non-toxic, pharmaceutically acceptable acid salts or mixtures thereof may be achieved parenterally, intravenously or orally. Typically, an effective amount of the derivative is combined with a suitable pharmaceutical carrier. As used herein, the term "effective amount" encompasses those amounts which yield the desired activity without causing adverse side-effects. The precise amount employed in a particular situation is dependent upon numerous factors such as method of administration, type of mammal, condition for which the derivative is administered, etc., and of course the structure of the derivative.

The pharmaceutical carriers which are typically employed with the derivatives of the present invention may be solid or liquid and are generally selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

The compounds of the invention are especially valuable as aromatase inhibiting agents and are therefore useful in the treatment of estrogen dependent diseases, e.g. breast cancer.

Estrogens are essential steroids in the physiology and function of normal development of breast and sex organs in women. On the other hand estrogens are known to stimulate the growth of estrogen dependent cancers, especially breast and endometrial cancers, and they may increase the risk of development of breast cancer if given at pharmacological doses for a long time.

Excessive production of estradiol may also cause other, benign disorders in hormone dependent organs. The importance of estrogens as cancer growth stimulators and/or regulators is clearly stressed by the fact that antiestrogens have reached a central position in the treatment of estrogen receptor rich breast cancers. Antiestrogens act by binding to estrogen receptors and thereby inhibiting the biological effects of estrogens. Another approach for blocking estrogen effect is to inhibit the synthesis of estrogens. This has been achieved clinically by the unspecific steroid synthesis inhibitor aminoglutethimide. The estrogen synthesis could be blocked specifically by inhibiting the enzyme aromatase, which is the key enzyme in biochemical estrogen synthesis pathway. Aromatase inhibition seems highly promising because several breast tumors synthesise estradiol and estrone in situ and exhibit therefore continuous growth stimulation (Alan Lipton et al., Cancer 59: 779-782, 1987).

Aromatase belongs to a group of cytochrome P450 enzymes, so called because terminal oxidase in the enzyme complex is the protein cytochrome P450. The P450 enzymes are important catalysts in many other steroid hormone syntheses. For example glucocorticoids and mineralocorticoids in the adrenal glands are synthesized through pathways in which specific P450 enzymes participate in rate-determining steps. Of particular importance in all steroidogenic tissues is the step of cholesterol side-chain cleavage, because cholesterol is a precursor for all steroid hormones. This cleavage step is catalysed by P450 scc, also know as desmolase. If desmolase is inhibited, there is a decrease in production of all steroid hormones, including gluco- and mineralocorticoids, with consequent side effects and problems. Different P450 enzymes show close homology, i.e., their structures including their active sites, tend to resemble one another. An inhibitor of one particular P450 enzyme is therefore likely to have the undesirable effect of inhibiting other P450 enzymes.

Perhaps the most important step in which aromatase inhibitors may cause inadvertent, undesirable inhibition is cholesterol side-chain cleavage. It is therefore important that aromatase inhibitors intended for treating estrogen-dependent diseases are selective.

The ability of the compounds of the invention to inhibit the enzyme aromatase was shown by the in vitro assay method according to M. Pasanen, Biological Research in Pregnancy, vol. 6, No. 2, 1985 (pp. 94–99). Human aromatase enzyme was used. The enzyme was prepared from human placenta, which is rich in the enzyme. Microsomal fraction (100000×g precipitate) was prepared by centrifugation. The enzyme preparation was used without further purification. Test compounds listed in Table 1 were added with 100000 dpm of 1,2[$^3$H]-androstene-3,17-dione and NADPH generating system. The concentrations of the test compounds were 0.001; 0.01; 0.1 and 1.0 mM. The incubation was carried out at 37° C. for 40 min. Aromatization of 1,2[$^3$H]-androstene-3,17-dione results in the production of $^3$H$_2$O. The tritiated water and the tritiated substrate are easily separated by a Sep-Pak ® minicolumn, which absorbs the steroid but allows free water elution. Radioactivity was counted by a liquid scintillation counter. Aromatase inhibition was evaluated by comparing the $^3$H$_2$O-radioactivity of inhibitor treated samples to controls containing no inhibitor. IC-10, IC-50 and IC-90 values were calculated as concentrations which inhibited the enzyme activity 10%, 50% and 90%, respectively. These concentrations are presented in Table 2.

Cholesterol side-chain cleavage activity (desmolase) was measured according to the method of Pasanen and Peklonen (Steroids 43: 517–527, 1984). Incubations were carried out in 1.5 ml Eppendorf plastic tubes, and an Eppendorf shaker, centrifuge and incubator were used as a unit. In a 300 μl incubation volume, the substrate (5 μM) was prepared according to Hanukoglu and Jefcoate (J. Chromatogr. 190: 256–262, 1980), and 100000 dpm of radioactive $^3$H-4-cholesterol (the purity of the compound was checked by TLC) in 0.5% Tween 20, 10 mM MgCl$_2$, 5 μm cyanoketone and 2 mM NADPH was added. Controls contained all the above substances but the enzyme preparation was inactivated prior to the incubation by the addition of 900 μl of methanol. The mitochondrial fraction (1 mg protein) from human placenta or bovine adrenals was used as a source of enzyme. After 30 min incubation at 37° C., the reaction was terminated by the addition of 900 μl of methanol; 1500 dpm of marker $^{14}$C-4-pregnenolone was added to each incubate and the tubes were vigorously shaken. After 10 min equilibration, the methanol-precipitated proteins were separated by the centrifugation (8000×g for 2 min) and the supernatant was sucked into 1 ml plastic injection syringe and loaded onto the pre-equilibrated (75% methanol) minicolumn.

The column was washed with one ml of 75% methanol and then with 3 ml of 80% methanol. The 80% methanol eluate was run into the counting vial and 10 ml of scintillation liquid was added. Radioactivity was counted using a double-label program on a liquid scintillation counter (LKB RackBeta). Typical activities for placental and bovine adrenal enzyme preparation were 0.5–3 and 50–100 pmol pregnenolone formed/mg protein/min, respectively.

In inhibition experiments, the test substance (final concentration range from 1 to 1000 μM) was added into the incubation mixture in a volume of 10–20 μl, as methanol or ethanol solution. The same volume of the solute was added into the control incubation vial. The IC-50 values (concentration causing a 50% inhibition) were determined graphically and are presented in Table 2.

TABLE 1

Compounds tested

| No. | Name |
|---|---|
| 1. | 4-[5-(2,6-dimethylphenyl)-3-hydroxy-3-(2,6-dimethylphenylethyl)pentyl]-1H-imidazole |
| 2. | 4-[3,3-bis(4-chlorophenyl)-3-hydroxypropyl]-1H-imidazole |
| 3. | 4-(3,3-diphenyl-3-hydroxypropyl)-1H-imidazole |
| 4. | 4-(3,3-diphenylpropen-2-yl)-1H-imidazole |
| 5. | 4-(3,3-diphenylpropyl)-1H-imidazole |
| 6. | 4-[3,3-bis(2-methylphenyl)-3-hydroxpropyl]-1H-imidazole |
| 7. | 4-[3,3-bis(4-chlorophenyl)propen-2-yl]-1H-imidazole |
| 8. | 4-[3,3-bis(2-methylphenyl)propen-2-yl]-1H-imidazole |
| 9. | 4-[3,3-bis(2-methylphenyl)propyl]-1H-imidazole |
| 10. | 1-benzyl-5-(3,3-diphenylpropyl)-1H-imidazole |
| 11. | 4-[3,3-bis(3-methylphenyl)propyl]-1H-imidazole |
| 12. | 4-[3,3-bis(3-methylphenyl)propen-2-yl]-1H-imidazole |
| 13. | 4-[3,3-bis(3-methoxyphenyl)propyl]-1H-imidazole |
| 14. | 4-[3,3-bis(2,3-dimethylphenyl)propyl]-1H-imidazole |
| 15. | 1-benzyl-5-[3,3-bis(3-methoxyphenyl)propyl]-1H-imidazole |
| 16. | 1-benzyl-5-[3,3-bis(3-methoxyphenyl)propen-2-yl]-1H-imidazole |
| 17. | 4-[3,3-bis(3,5-dimethylphenyl)propyl]-1H-imidazole |
| 18. | 4-[3,3-bis(4-methylphenyl)propyl]-1H-imidazole |
| 19. | 4-[3,3-bis(3-fluorophenyl)propyl]-1H-imidazole |
| 20. | 1-benzyl-5-(3,3-diphenylpropen-2-yl)-1H-imidazole |
| 21. | 1-benzyl-5-(3,5-diphenylpentyl)-1H-imidazole |
| 22. | 4-[3,3-bis(4-methoxyphenyl)propyl]-1H-imidazole |
| 23. | 4-(3,4-diphenylbutyl)-1H-imidazole |
| 24. | 4-[3-(4-methylphenyl)-3-phenylpropyl]-1H-imidazole |
| 25. | 4-[3,3-bis(2-methoxyphenyl)propyl]-1H-imidazole |
| 26. | 4-[3-(4-fluorophenyl)-3-phenylpropyl]-1H-imidazole |
| 27. | 4-[3,3-bis(4-fluorophenyl)propyl]-1H-imidazole |
| 28. | 1-benzyl-5-(3,3-diphenylpropen-1-yl)-1H-imidazole |

TABLE 2

Inhibition of human aromatase and desmolase by test compounds. IC-10, IC-50 and IC-90 represent the concentration which inhibit the enzyme by 10%, 50% and 90% respectively.

| COMPOUND No. | AROMATASE | | | DESMOLASE |
|---|---|---|---|---|
| | IC-10 mmol/l | IC-50 mmol/l | IC-90 mmol/l | IC-50 mmol/l |
| 1 | 0.02 | 1.0 | >1 | |
| 2 | 0.004 | 0.06 | 1.0 | |
| 3 | 0.004 | 0.07 | 1.0 | |
| 4 | <0.001 | 0.006 | 0.10 | |
| 5 | 0.0015 | 0.015 | 0.40 | 0.036 |
| 6 | 0.015 | 0.30 | >1 | |
| 7 | 0.002 | 0.035 | 0.6 | 0.130 |
| 8 | 0.0015 | 0.080 | >1 | |
| 9 | 0.002 | 0.030 | 0.6 | |
| 10 | ~0.0006 | 0.004 | 0.10 | |
| 11 | ~0.0006 | 0.002 | 0.10 | 0.029 |
| 12 | 0.001 | 0.062 | 1 | |
| 13 | | 0.003 | | 0.036 |
| 14 | | 0.044 | | 0.086 |
| 15 | | 0.004 | | |
| 16 | | 0.014 | | 0.022 |
| 17 | | 0.130 | | |
| 18 | | 0.014 | | 0.048 |
| 19 | | 0.019 | | 0.020 |
| 20 | | 0.050 | | |
| 21 | | 0.017 | | 0.031 |
| 22 | | 0.0086 | | 0.026 |
| 23 | | 0.0075 | | 0.019 |
| 24 | | 0.007 | | 0.050 |
| 25 | | 0.0086 | | 0.032 |
| 26 | | 0.0101 | | 0.440 |
| 27 | | 0.005 | | 0.030 |
| 28 | | 0.014 | | 0.110 |

The ability of the Eli Lilly compound, 4-(2,2-diphenylethyl)-1H-imidazole to inhibit aromatase and desmolase was tested according to the methods described above. The aromatase and desmolase inhibition activities are compared with the closest compound of the present invention, 4-(3,3-diphenylpropyl)-1H-imidazole, in Table 3.

TABLE 3

Inhibition of human aromatase and desmolase by 4-(2,2-diphenylethyl)-1H-imidazole and 4-(3,3-diphenylpropyl)-1H-imidazole. IC-50 represent the concentration which inhibit the enzyme by 50%.

| COMPOUND | AROMATASE IC-50 $\mu mol/l$ | DESMOLASE IC-50 $\mu mol/l$ |
|---|---|---|
| 4-(2,2-diphenylethyl)-1H-imidazole | 49 | 9 |
| 4-(3,3-diphenylpropyl)-1H-imidazole | 15 | 36 |

The results show that the compound of the invention is a selective aromatase inhibitor and the prior art compound does not inhibit selectively aromatase. According to the results the prior art compound is a selective desmolase inhibitor.

The daily dose for a patient varies from about 20 to about 200 mg, administered orally.

The toxicity of the imidazole derivatives of the present invention was studied in rats. There were 5 female rats in each drug group and dosing was carried out during 8 days. The dose level used was 10 mg/kg/day orally. The derivatives tested were 4-(3,3-diphenylpropen-2-yl)-1H-imidazole, 4-(3,3-diphenylpropyl)-1H-imidazole, 4-[3,3-bis(2-methylphenyl)propyl]-1H-imidazole, 1-benzyl-5-(3,3-diphenylpropyl)-1H-imidazole and 1-benzyl-5-(3,3-diphenylpropen-2-yl)-1H-imidazole.

The behaviour, appearance and mortality of the animals were followed daily. The animals were weighed before and after dosing period. The organs were examined macroscopically at autopsy. The liver, uterus and ovaries were weighed. No mortality were observed. The weight development was normal in all groups. In the groups that were treated with 4-(3,3-diphenylpropen-2-yl)-1H-imidazole and 1-benzyl-5-(3,3-diphenylpropen-2-yl)-1H-imidazole a slight piloerection was observed propably as pharmacological effects of the drugs. No drug-related findings were observed in organ weights or in macroscopical pathology. In conclusion, all studied compounds were well tolerated.

The following examples illustrate the invention.

EXAMPLE 1

4-(3,3-diphenyl-3-hydroxypropyl)-1H-imidazole a) 5-(1-benzylimidazole)acrylic acid In a flask are placed 18,6 g of 5-(1-benzylimidazole)-carbaldehyde, 10,4 g of malonic acid, and 4,8 ml of pyridine. The mixture is heated on a boiling water bath for 16 hours. It is then cooled and diluted with water. The precipitate which is the product is filtered and washed with water. Yield 15 g. M.p. 221°-226° C.

$^1$H NMR: 5.15 (s, 1H), 5.64 (s, 2H), 6.58 (d, 1H), 7.3-7.5 (m, 5H), 7.61 (d, 1H), 8.08 (s, 1H), 9.07 (s, 1H).

b) 4(5)-imidazole propionic acid ethyl ester 5-(1-benzylimidazole)acrylic acid (15 g) is dissolved in 50 ml of 4-N hydrochloric acid. About 60 mg of 10% Pd/C are added and the mixture is stirred vigorously under a hydrogen atmosphere at about 85° C. until no more hydrogen is consumed. The reaction mixture is then filtered and evaporated to dryness.

The residue is dissolved in 50 ml of abs, ethanol and dry hydrogen chloride gas is passed into the solution for 4 hours during which time the reaction mixture is maintained at reflux with stirring. The mixture is then evaporated to dryness to give an oily residue which is a crude product useful as such in the following Grignard reaction.

$^1$H NMR: 1.237 (t, 3H), 2.656 (t, 2H), 2.936 (t, 2H), 4.137 (q, 2H), 6.804 (s, 1H), 7.559 (s, 1H).

c) 4-(3,3-diphenyl-3-hydroxypropyl)-1H-imidazole 3,3 g of magnesium turnings are covered with 100 ml of dry tetrahydrofuran. To that mixture is then added dropwise a solution of 21,8 g of bromobenzene in 30 ml of dry tetrahydrofuran at such a rate that a smooth reaction is maintained. After the addition is complete, the reaction mixture is refluxed for one additional hour and cooled to room temperature. The reaction mixture is then added dropwise to a solution of 4(5)-imidazole propionic acid ethyl ester (7,8 g) in 50 ml of tetrahydrofuran at room temperature. After the addition is complete, the reaction mixture is stirred for an additional hour at 40°-50° C. The mixture is then cooled and poured into cold water. Tetrahydrofuran is evaporated and to the solution is added conc. hydrochloric acid (20 ml). The solution is cooled and the precipitate which contains the product as hydrochloride salt is removed by filtration, washed and dried. Yield 11,2 g. M.p. 189°-191° C.

$^1$H NMR: 2.703 (s, 4H), 4.758 (s, 3H), 7.214-7.429 (m, 11H), 8.457 (s, 1H).

In the same way, via the Grignard reaction starting from 4(5)-imidazole propionic acid ethyl ester and from proper substituted bromobenzene, can also be prepared other compounds of the invention.

For example the following substituted derivatives were prepared:

4-[3,3-bis(4-chlorophenyl)-3-hydroxypropyl]-1H-imidazole. M.p. of hydrochloride 85°-89° C.

4-[3,3-bis(2-methylphenyl)-3-hydroxypropyl]-1H-imidazole. M.p. of hydrochloride 211°-213° C.

4-[3,3-bis(3-methylphenyl)-3-hydroxypropyl]-1H-imidazole. M.p. of hydrochloride 170°-172° C.

EXAMPLE 2

4-(3,3-diphenylpropen-2-yl)-1H-imidazole 2,0 g of 4-(3,3-diphenyl-3-hydroxypropyl)-1H-imidazole hydrochloride is mixed with 20 g of anhydrous potassium hydrogen sulfate and the mixture is warmed on an oil bath at 150°-155° C. for 4 hours. The mixture is then cooled and 20 ml water is added. The mixture is made alkaline with sodium hydroxide solution and cooled. The precipitate, which is the product, is filtered, washed with water and dried. Yield 1,25 g. After recrystallization from water-ethanol, the product melts at 124°-128° C.

$^1$H NMR: 3.42 (d, 2H), 4.756 (s, 1H), 6.284 (t, 1H), 6.768 (s, 1H), 7.2-7.4 (m, 10H), 7.559 (s, 1H).

According to the same procedure for example the following substituted derivatives were prepared:

4-[3,3-bis(4-chlorophenyl)propen-2-yl]-1H-imidazole hydrochloride. M.p. 158°-163° C.

4-[3,3-bis(2-methylphenyl)propen-2-yl]-1H-imidazole hydrochloride. M.p. 195°-198° C.

4-[3,3-bis(3-methylphenyl)propen-2-yl]-1H-imidazole. M.p. 115°-118° C.

4-[3,3-bis(3-fluorophenyl)propen-2-yl]-1H-imidazole. M.p. of hydrochloride is 125°-128° C.

EXAMPLE 3

4-(3,3-diphenylpropyl)-1H-imidazole 4-(3,3-diphenylpropen-2-yl)-1H-imidazole (0,7 g) is dissolved in ethanol and a catalytic amount of Pd/C (10%) is added. The reaction mixture is agitated vigorously at room temperature in a hydrogen atmosphere until the uptake of hydrogen ceases. The mixture is filtered and the filtrate is evaporated to dryness. The residue is recrystallized from water-ethanol mixture. Yield 0,4 g, m.p. 115°-117° C.

$^1$H NMR: 2.3-2.5 (m, 4H), 3.919 (t, 1H), 4.752 (s, 1H), 6.708 (s, 1H), 7.1-7.3 (m, 10H), 7.532 (s, 1H).

According to the same procedure as the example the following substituted derivatives were prepared:

4-[3,3-bis(2-methylphenyl)propyl]-1H-imidazole, hydrochloride. M.p. 84°-87° C.

4-[3,3-bis(3-methylphenyl)propyl]-1H-imidazole. M.p. 111°-114° C.

$^1$H NMR (as base): 2.272 (s, 6H), 2.2-2.5 (m, 4H), 3.823 (t, 1H), 6.691 (s, 1H), 6.8-7.2 (m, 8H), 7.440 (s, 1H).

4-[3,3-bis(3-fluorophenyl)propyl]-1H-imidazole $^1$H NMR (as HCl): 2.3-2.8 (m, 4H), 4.060 (t, 1H), 4.784 (s, 2H), 6.7-7.4 (m, 9H), 8.743 (s, 1H).

EXAMPLE 4

1-benzyl-5-[3,3-bis(4-chlorophenyl)-3-hydroxypropyl]-1H-imidazole a) 1-benzyl-5-imidazole acrylic acid methyl ester In a flask are placed 12,0 g of 5-(1-benzylimidazole)acrylic acid (prepared in example 1), 70 ml of methanol and dry hydrogen chloride gas is passed into the solution for 4 hours, during which time the reaction mixture is maintained at reflux. The mixture is then evaporated to dryness and the residue is dissolved in cold water. The solution is then made alkaline with sodium carbonate and the precipitate, which is the product, is filtered, washed with water and dried. Yield 12,2 g; m.p. 137°-139° C.

$^1$H NMR: 3.781 (s, 3H), 5.490 (s, 2H), 6.452 (d, 1H), 7.2-7.5 (m, 5H), 7.493 (d, 1H), 7.710 (s, 1H), 8.083 (s, 1H).

b) 1-benzyl-5-imidazole propionic acid methyl ester

The double bond of the side chain is hydrogenated in abs. ethanol Pd/C as catalyst. When the uptake of hydrogen ceases, the reaction mixture is filtered and the filtrate is evaporated to dryness. The residue is dissolved in methylene chloride, which is washed with water. Methylene chloride phase is then dried and evaporated to dryness to give the product, which is used as such in the accompanying Grignard reactions.

$^{13}$C NMR: Aliphatic carbons are detected at ppm: 19.374, 32,573, 48.466, 51.675; aromatic carbons are detected at ppm: 126.569, 128.022, 128.748, 128.960, 130.474, 136.074, 137.88; and carbonyl at ppm: 172.522.

c) 1-benzyl-5-[3,3-bis(4-chlorophenyl)-3-hydroxypropyl]-1H-imidazole

The Grignard reagent is prepared from 2,4 g of magnesium turnings and from 19,1 g of p-chlorobromobenzene in tetrahydrofuran as is described in Example 1 c).

1-benzyl-5-imidazole propionic acid methyl ester (6,4 g) in tetrahydrofuran is heated at 60° C. and to this is then added dropwise p-chlorophenylmagnesium bromide prepared above. After the addition is complete, the reaction mixture is refluxed for an additional 3 hours, cooled and poured into cold water. Tetrahydrofuran is evaporated, toluene is added and the mixture is made acidic with hydrochloric acid. The precipitated product is filtered, washed with ether and dried. Yield 12,2 g; m.p. 210°-213° C. M.p. of nitrate 157°-160° C. (made in water-ether mixture). M.p. of hydrochloride (from ethylacetate) 178°-187° C.

$^1$H NMR: 2.985 (s, 4H), 4.854 (s, 2H), 5.330 (s, 2H), 7.06-7.46 (m, 14H), 8.993 (s, 1H).

Other 1-benzyl substituted derivatives are also prepared in the same way. For example:

1-benzyl-5-[5-(2,6-dimethylphenyl)-3-hydroxy-3-(2,6-dimethylphenylethyl)penthyl]-1H-imidazole from 1-benzyl-5-imidazole propionic acid methyl ester and 2-(2,6-dimethylphenyl)ethylmagnesium bromide. Melting point of the hydrochloride is 67°-71° C.

EXAMPLE 5

1-benzyl-5-[3,3-bis(4-chlorophenyl)propen-2-yl]-1H-imidazole 4,1 g of 1-benzyl-5-[3,3-bis(4-chlorophenyl)-3-hydroxypropyl]-1H-imidazole and 22,0 g of anhydrous potassium hydrogen sulfate are heated at 150° C. for 4 hours. The mixture is cooled, 100 ml of ethanol is added to dissolve the product. The mixture is then filtered and the filtrate is evaporated to minor volume. Water is added and the mixture is made basic with sodium hydroxide. The precipitate, which is the product, is filtered, washed with water and dried. The product is recrystallized from water-ethanol. Yield 2,3 g. Nitrate is made in water with nitric acid.

$^1$H NMR: 3,293 (d, 2H), 5.287 (s, 1H), 6.010 (t, 1H), 6.9-7.4 (m, 14H), 9.330 (s, 1H).

EXAMPLE 6

4-[3-(4-chlorophenyl)-3-hydroxy-3-phenylpropyl]-1H-imidazole a) 3-(4-imidazolyl)ethyl 4-chlorophenyl ketone 0,85 g of magnesium turnings are covered with 20 ml of dry tetrahydrofuran, the mixture is heated to boiling and to it is added 6,8 g of 4-bromochlorobenzene in tetrahydrofuran at such a rate that a smooth reaction is maintained. After the addition is complete, the reaction mixture is refluxed for one additional hour. The reaction mixture is then cooled and added dropwise at room temperature to a solution of 4(5)-imidazole propionic acid ethyl ester (4,0 g) in tetrahydrofuran. After addition the reaction mixture is stirred for an additional hour at room temperature. It is then poured into cold water and made acidic with hydrochloric acid. The reaction mixture is then washed with methylene chloride, made alkaline with sodium hydroxide, and the product is extracted to methylene chloride. Yield 2,2 g. Hydrochloride salt is made in conc. hydrochloric acid. M.p. 160°-161° C.

b) 4-[3-(4-chlorophenyl)-3-hydroxy-3-phenylpropyl]-1H-imidazole

Phenylmagnesiumbromide is made in tetrahydrofuran from 0,51 g of magnesium turnings and 3,3 g of bromobenzene. 3-(4-imidazolyl)-ethyl 4-chlorophenyl ketone (2,3 g) is dissolved in tetrahydrofuran and phenylmagnesiumbromide is dropped to that solution at room temperature. After addition the reaction mixture is stirred at 40°-50° C. for additional 3 hours. It is then cooled and poured into cold water. Water is made acidic with hydrochloric acid. The product is extracted into methylenechloride, which is evaporated into dryness. The product as hydrochloride is recrystallized from water-ethanol. Yield 3,2 g.

EXAMPLE 7

1-benzyl-4-(3,3-diphenylpropyl)-1H-imidazole and 1-benzyl-5-(3,3-diphenylpropyl)-1H-imidazole 4-(3,3-diphenylpropyl)-1H-imidazole (2,6 g) is dissolved in 6 ml of dry dimethylformamide. While stirring 0,5 g of NaH (60%) is added during half an hour at room temperature. After addition the reaction mixture is stirred additional one hour. 1,7 g of benzylbromide in 3 ml of dimethylformamide is then dropped at room temperature and stirring is continued for 4 hours. The reaction mixture is poured to cold water (30 ml) and the mixture is extracted with toluene. Toluene extracts are then washed with water and evaporated to dryness. The residue, which is the mixture of products, is purified and separated to pure isomers by column chromatography (methylene chloride/methanol, 9,5/0,5).

$^1$H NMR of the products:
One of the isomers: 2.57 (m, 4H), 3.52 (1H), 3,877 (t, 1H), 5.362 (s, 2H), 6.531 (s, 1H), 7.05-7.40 (m, 15H), 9.567 (s, 1H).

The other isomer: 2.375 (m, 4H), 3.858 (t, 1H), 5.253 (s, 2H), 7.01-7.36 (m, 16H), 9.441 (s, 1H).

EXAMPLE 8

1-(4-chlorobenzyl)-4-(3,3-diphenylpropyl)-1H-imidazole and
1-(4-chlorobenzyl)-5-(3,3-diphenylpropyl)-1H-imidazole The compounds were prepared in the same way as the compounds in Example 7 starting from 4-(3,3-diphenylpropyl)-1H-imidazole and 4-chlorobenzylchloride.

$^1$H NMR of the products:
One isomer: 2.48 (m, 4H), 3.934 (t, 1H), 4.999 (s, 2H), 6.514 (s, 1H), 7.0-7.3 (m, 14H), 7.517 (s, 1H).
The other isomer: 2.33 (m, 4H), 3.887 (t, 1H), 4.852 (s, 2H), 6.7-7.5 (m, 16H).

EXAMPLE 9

4-[5-(2,6-dimethylphenyl)-3-(2,6-dimethylphenylethyl)pentyl]-1H-imidazole 4,0 g of 1-benzyl-5-[5-(2,6-dimethylphenyl)-3-hydroxy-3-(2,6-dimethylphenylethyl)pentyl]-1H-imidazole hydrochloride and 20 g of kalium hydrogen sulfate is combined and the mixture is heated for 6 hours at 150° C. Ethanol (40 ml) is added and the mixture is filtered. 20 ml of conc. hydrochloric acid is added and the mixture is hydrogenated palladium on carbon (10%) as catalyst until the hydrogen consumption ceases. The reaction mixture is filtered, water is added and the mixture is made alkaline with sodium hydroxide. The product is then extracted into toluene, which is washed with water, and evaporated to dryness. The residue which is the product as base, is converted to nitrate with nitric acid in water. M.p. 147°-150° C.

EXAMPLE 10

4-[3,3-bis(3,5-dimethylphenyl)propyl]-1H-imidazole a) 1-benzyl-5-[3,3-bis(3,5-dimethylphenyl)-3-hydroxypropyl]-1H-imidazole 1,06 g of magnesium turnings are covered with 30 ml of dry tetrahydrofuran. To the mixture is then added dropwise a solution of 5-bromo-m-xylene (8,14 g) in 10 ml of dry tetrahydrofuran at such a rate that a smooth reaction is maintained. After the addition is complete, the reaction mixture is refluxed for one additional hour and cooled to room temperature. The reaction mixture is then added dropwise to a solution of 1-benzyl-5-imidazole propionic acid ethyl ester (5,0 g) in 40 ml of tetrahydrofuran at 60° C. After the addition is complete, the reaction mixture is refluxed for 2 hours, cooled and poured into cold water. Tetrahydrofuran is evaporated and to the solution is added conc. hydrochloric acid. The solution is cooled, some ether is added and the precipitate which contains the product as hydrochloride salt is removed by filtration, washed and dried. Yield 4,1 g. M.p. 120°-124° C.

b) 1-benzyl-5-[3,3-bis(3,5-dimethylphenyl)propen-2-yl]-1H-imidazole 4,0 g of 1-benzyl-5-[3,3-bis(3,5-dimethylphenyl)-3-hydroxypropyl]-1H-imidazole is dissolved in 30 ml of ethanol and 2 ml of conc. hydrochloric acid is added. The reaction mixture is then refluxed for 4 hours and evaporated to dryness. The residue which is the product is recrystallized from ethyl acetate. Yield 3,1 g. M.p. 170°-176° C.

According to the same procedure as the example the following substituted derivatives were prepared:
1-benzyl-5-(3,3-diphenylpropen-2-yl)-1H-imidazole, hydrochloride. M.p. 173°-175° C.
1-benzyl-5-[3,3-bis(2-methoxyphenyl)propen-2-yl]-1H-imidazole, hydrochloride. M.p. 191°-197° C. 1-benzyl-5-[3,3-bis(3-methoxyphenyl)propen-2-yl]-1H-imidazole, hydrochloride. M.p. 132°-135° C.
1-benzyl-5-[3,3-bis(4-methoxyphenyl)propen-2-yl]-1H-imidazole, hydrochloride. M.p. 157°-163° C.
1-benzyl-5-[3,3-bis(2,3-dimethylphenyl)propen-2-yl]-1H-imidazole, hydrochloride.

$^1$H NMR (as base): 2.055 (s, 3H), 2.159 (s, 3H), 2.251 (s, 6H), 3.467 (d, 2H), 4.781 (s, 1H), 5.281 (s, 2H), 5.761 (t, 1H), 6.8-7.4 (m, 12H), 9.97 (s, 1H)
1-benzyl-5-[3,3-bis(2-methylphenyl)propen-2-yl]-1H-imidazole, hydrochloride. M.p. 84°-87° C.
1-benzyl-5-[3,3-bis(3-methylphenyl)propen-2-yl]-1H-imidazole, hydrochloride. M.p. 115°-117° C.

c) 1-benzyl-5-[3,3-bis(3,5-dimethylphenyl)propyl]-1H-imidazole 1-benzyl-5-[3,3-bis(3,5-dimethylphenyl)propen-2yl]-1H-imidazole hydrochloride is dissolved in ethanol and a catalytic amount of Pd/C (10%) is added. The reaction mixture is agitated vigorously at room temperature in a hydrogen atmosphere until the uptake of hydrogen ceases. The mixture is filtered and the filtrate is evaporated to dryness. The residue which is the product is purified by flash chromatography eluating with methylene chloride-methanol mixture.

By the same method is prepared for example 1-benzyl-5-[3,3-bis(3-methoxyphenyl)propyl]-1H-imidazole hydrochloride, m.p. 165°-167° C., and 1-benzyl-5-[3,3-diphenylpropyl]-1H-imidazole hydrochloride, m.p. 160°-162° C.

d) 4-[3,3-bis(3,5-dimethylphenyl)propyl]-1H-imidazole 2,0 g of 1-benzyl-5-[3,3-bis(3,5-dimethylphenyl)propyl]-1H-imidazole hydrochloride is hydrogenated in the mixture of 30 ml of 2N hydrochloric acid and 10 ml ethanol at 80° C. Pd/C (10%) as catalyst. When the uptake of hydrogen ceases, the reaction mixture is cooled, filtered and evaporated to dryness. Water is added and the mixture is made alkaline with sodium hydroxide. The product is then extracted to ethylacetate which is washed with water, dried with sodium sulfate and evaporated to dryness. The residue is the product as base and it is made to its hydrochloride salt in ethyl acetate using dry hydrochloric acid. Yield 0,6 g. M.p. of the product is 101°–105° C.

$^1$H NMR: 2.247 (s, 12H), 2.2–3.7 (m, 4H), 3.798 (t, 1H), 4.788 (s, 2H), 6.8–7.2 (m, 6H), 7.214 (s, 1H), 8.715 (s, 1H).

Using the same method for example the following compounds included in the invention were prepared:

4-[3,3-bis(2,3-dimethylphenyl)propyl]-1H-imidazole $^1$H NMR (as base): 2.097 (s, 6H), 2.260 (s, 6H), 2.3 (m, 2H), 2.6 (m, 2H), 4.389 (s, 1H), 6.0 (s, 1H), 6.712 (s, 1H), 7.011 (s, 6H), 7.508 (s, 1H).

4-[3,3-bis(2-methoxyphenyl)propyl]-1H-imidazole, hydrochloride. M.p. 194°–196° C.

4-[3,3-bis(3-methoxyphenyl)propyl]-1H-imidazole $^1$H NMR (as base): 2.5 (m, 4H), 3.747 (s, 6H), 3.862 (t, 1H), 6.6–7.3 (m, 9H), 7.498 (s, 1H), 8.165 (s, 1H).

4-[5-(2,6-dimethylphenyl)-3-hydroxy-3-(2,6-dimethylphenylethyl)pentyl]-1H-imidazole, hydrochloride. M.p. 178°–180° C.

4-[3,3-bis(4-methoxyphenyl)propyl]-1H-imidazole $^1$H NMR (as base): 2.5 (m, 4H), 3.744 (s, 6H), 3.815 (t, 1H), 6.1 (broad signal, 1H), 6.732–7.171 (m, 9H), 7.489 (s, 1H).

4-[3,3-bis(4-methylphenyl)propyl]-1H-imidazole $^1$H NMR (as hydrochloride): 2.260 (s, 6H), 2.5 (m, 4H), 3.879 (t, 1H), 4.907 (s, 2H), 6.9–7.2 (m, 9H), 8.727 (s, 1H).

EXAMPLE 11

1-benzyl-5-[3,3-bis(4-methylphenyl)propen-2-yl]-1H-imidazole

To a dry flask is placed 4,8 g (0,2 mol) of NaH (washed free from oil with cyclohexane). Onto it is then dropped 100 ml of dry dimethylsulfoxide. The reaction vessel is warmed at 80° C. until the evolution of hydrogen ceases. The resulting solution of methylsulfinyl carbanion is cooled in an ice-water bath and 54,1 g of 3-(1-benzyl-5-imidazolyl)-ethyltriphenylphosphonium bromide is added in 200 ml of dimethylsulfoxide. The reaction mixture is then stirred at room temperature for 0.5 hours and to it is added in small portions 23,0 g of 4,4'-dimethylbenzophenone. The reaction mixture is stirred at room temperature for 1 hour and some of the dimethylsulfoxide is distilled. The residue is poured into water which is made alkaline with sodium hydroxide. The product is extracted into toluene which is washed with water, dried with sodium sulfate and evaporated to dryness. From the residue which contains the crude product as base is converted into the hydrochloride in ethylacetate. Yield 32 g. M.p. 216°–220° C.

$^1$H NMR: 2.289 (s, 3H), 2.370 (s, 3H), 3.467 (d, 2H), 4.764 (s, 1H), 5.302 (s, 2H), 6.030 (t, 1H), 6.8–7.4 (m, 9H), 8.9 (s, 1H)

EXAMPLE 12

4-(3,4-diphenylbutyl)-1H-imidazole a) 1-benzyl-4-(3,4-diphenyl-3-hydroxybutyl)-1H-imidazole Grignard reagent is made from benzylchloride and magnesium in diethyl ether and the Grignard reaction is carried out as described in the example 6b) using 1-benzyl-3-(4-imidazolyl)-ethylketone as the starting compound.

b) 4-(3,4-diphenylbutyl)-1H-imidazole

The dehydration of 1-benzyl-4-(3,4-diphenyl-3-hydroxybutyl)-1H-imidazole and the hydrogenation are carried out as described in the Example 9. The product as base is purified by flash chromatography. The product may be made to its hydrochloride salt in ethyl acetate using dry hydrochloric acid.

$^1$H NMR (as base): 1.8–2.2 (m, 2H), 2.39 (m, 2H), 2.8–3.0 (m, 3H), 6.4 (s, 1H), 6.62 (s, 1H), 6.8–7.3 (m, 10H), 7.45 (s, 1H).

Using the same method the following compound included in the invention were prepared:

4-[3-(4-methylphenyl)-3-phenylpropyl]-1H-imidazole $^1$H NMR (as base): 2.279 (t, 3H), 2.3–2.6 (m, 4H), 3.88 (t, 1H), 6.719 (s, 1H), 7.09 (s, 5H), 7.21 (m, 4H), 7.48 (s, 1H).

4-(3,5-diphenylpentyl)-1H-imidazole $^1$H NMR (as base): 1.7–2.2 (m, 4H), 2.3–2.7 (m, 5H), 6.1 (s, 1H), 6.66 (s, 1H), 6.9–7.3 (m, 10H), 7.46 (s, 1H).

4-[3-(4-fluorophenyl)-3-phenylpropyl]-1H-imidazole $^1$H NMR (as hydrochloride): 2.40–2.49 (m, 2H), 2.65–2.70 (m, 2H), 3.995 (t, 1H), 6.98–7.34 (m, 10H), 8.766 (d, 1H).

4-[3,3-bis(4-fluorophenyl)propyl]-1H-imidazole, hydrochloride. M.p. 135°–139° C.

EXAMPLE 13

1-benzyl-5-(3,3-diphenylpropen-1-yl)-1H-imidazole a) 1-benzyl-5-(3,3-diphenyl-1-hydroxypropyl)-1H-imidazole The Gringnard reagent, diphenylethanyl magnesium chloride, is prepared by the usual way from diphenylethanylchloride (0.01 mol) and magnesium turnings (0.01 mol) in dry diethylether (30 ml). 1-benzyl-5-imidazole aldehyde (0.005 mol) is dissolved in dry diethylether and the Grignard reagent is added dropwise to the solution. The reaction mixture is refluxed for 3 hours. The reaction is then poured into 2N hydrochloric acid and extracted with diethylether. The water phase is made basic with sodium hydroxide and then extracted with ethyl acetate. The ethyl acetate phase is dried and evaporated. The residue is purified by flash-chromatography eluating with methylene chloride-methanol mixture (9.5:0.5). M.p. of the product as base is 188°–190° C.

$^1$H NMR (as base): 2.53 (t, 2H), 4.16 (t, 1H), 4.38 (t, 1H), 4.99 and 5.09 (ABq, 2H), 6.9–6.95 (m, 2H), 7.02 (s, 1H), 7.14–7.27 (m, 13H), 7.43 (s, 1H).

b) 1-benzyl-5-(3,3-diphenylpropen-1-yl)-1H-imidazole 1-benzyl-(3,3-diphenyl-1-hydroxypropyl)-1H-imidazole (0.01 mol) and potassium hydrogen sulfate (0.135 mol) are combined and the mixture is heated for 6 hours in an oil bath at 155° C. with stirring now and then. The reaction mixture is allowed to cool, made basic with 2M sodium hydroxide and extracted with methylene chloride. The methylene chloride phase is dried and evaporated. The residue is purified by flash-chromatography eluting with methylene chloride-methanol mixture (9.5:0.5). The product as base is made to its hydrochloride salt in diethylether using dry hydrogen chloride gas.

$^1$H NMR (as base): 4.90 (d, 1H), 5.39 (s, 2H), 6.09 (d, 1H), 6.82 (dd, 1H), 7.0–7.4 (m, 15H), 7.74 (s, 1H), 9.03 (s, 1H).

We claim:

1. A substituted imidazole of the formula:

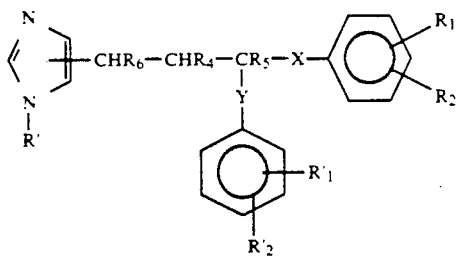 (I)

or a non-toxic pharmaceutically acceptable acid addition salt thereof wherein $R_1$, $R_2$, $R'_1$ and $R'_2$, which can be the same or different, are H, $CH_3$, $C_2H_5$, $OCH_3$, OH, $CH_2OH$, $NH_2$ or halogen; R' is H or

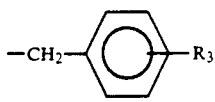

where $R_3$ is H, $CH_3$ or halogen; $R_4$ is H, $R_5$ is H or OH and $R_6$ is H or OH or one of $R_5$ and $R_6$ is H and the other, together with $R_4$, forms a bond and X and Y, which can be the same or different, are a bond, a straight $C_{1-2}$-alkyl or the corresponding alkenyl.

2. A substituted imidazole of the formula:

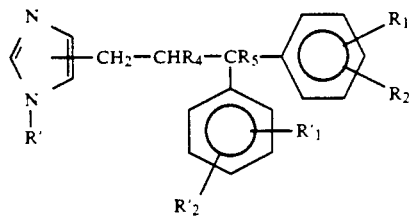

or a non-toxic pharmaceutically acceptable acid addition salt thereof wherein $R_1$, $R_2$, $R'_1$ and $R'_2$, which can be the same or different are H, $CH_3$, $C_2H_5$, $OCH_3$, OH, $CH_2OH$, $NH_2$ or halogen; R' is H or

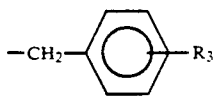

where $R_3$ is H, $CH_3$ or halogen; $R_4$ is H and $R_5$ is H or $R_4$ and $R_5$ together form a bond.

3. A substituted imidazole according to claim 2 wherein $R_4$ and $R_5$ are both H.

4. A substituted imidazole according to claim 3 wherein at least one of $R_1$, $R_2$, $R'_1$ and $R'_2$ is not H and one or more of the substituents $R_1$, $R_2$, $R'_1$ and $R'_2$ are in the 3, 4, 5, 3', 4' or 5' positions of the phenyl groups.

5. A substituted imidazole according to claim 3 wherein $R_2$ and $R'_2$ both are H and $R_1$ and $R'_1$ are both not H and are both in the meta position of the phenyl groups.

6. A substituted imidazole according to claim 3 wherein $R_2$ and $R'_2$ both are H and $R_1$ and $R'_1$ are both not H and are both in the para position of the phenyl groups.

7. A substituted imidazole according to claim 3 wherein $R_2$, $R'_2$ and $R'_1$ each are H and $R_1$ is not H and is in the para position of the phenyl group.

8. A substituted imidazole according to claim 2 wherein $R_4$ and $R_5$ together form a bond.

9. A substituted imidazole according to claim 8 wherein $R_2$ and $R'_2$ both are H and $R_1$ and $R'_1$ are both not H and are both in the meta position of the phenyl groups.

10. A substituted imidazole according to claim 8 wherein $R_2$ and $R'_2$ both are H and $R_1$ and $R'_1$ are both not H and are in the para position of the phenyl groups.

11. A substituted imidazole according to claim 2 wherein R' is H.

12. A substituted imidazole according to claim 2 wherein R' is

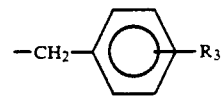

where $R_3$ is H, $CH_3$ or halogen.

13. A substituted imidazole according to claim 12 wherein $R_3$ is H.

14. A compound according to claim 1 which is
4-[5-(2,6-dimethylphenyl)-3-hydroxy-3-(2,6-dimethylphenylethyl)pentyl]-1H-imidazole,
4-[3,3-bis(4-chlorophenyl)-3-hydroxypropyl]-1H-imidazole,
4-[3,3-diphenyl-3-hydroxypropyl]-1H-imidazole,
4-[3,3-diphenylpropen-2-yl]-1H-imidazole,
4-[3,3-diphenylpropyl]-1H-imidazole,
4-[3,3-bis(2-methylphenyl)-3-hydroxypropyl]-1H-imidazole,
4-[3,3-bis(4-chlorophenyl)propen-2-yl]-1H-imidazole,
4-[3,3-bis(2-methylphenyl)propen-2-yl]-1H-imidazole,
4-[3,3-bis(2-methylphenyl)propyl]-1H-imidazole,
1-benzyl-4-(3,3-diphenylpropyl)-1H-imidazole,
1-benzyl-5-(3,3-diphenylpropyl)-1H-imidazole,
4-[3,3-bis(3-methylphenyl)propyl]-1H-imidazole,
4-[3,3-bis(3-methylphenyl)propen-2-yl]-1H-imidazole,
1-(4-chlorobenzyl)-4-(3,3-diphenylpropyl)-1H-imidazole,
1-(4-chlorobenzyl)-5-(3,3-diphenylpropyl)-1H-imidazole,
4-[5-(2,6-dimethylphenyl)-3-(2,6-dimethylphenylethyl)-pentyl]-1H-imidazole,
4-[3,3-bis(3,5-dimethylphenyl)propyl]-1H-imidazole,
4-[3,3-bis(3-methoxyphenyl)propyl]-1H-imidazole,
4-[3,3-bis(2,3-dimethylphenyl)propyl]-1H-imidazole,
1-benzyl-5-[3,3-bis(3-methoxyphenyl)propyl]-1H-imidazole,
1-benzyl-5-[3,3-bis(3-methoxyphenyl)propen-2-yl]-1H-imidazole,
1-benzyl-5-[3,3-bis(3,5-dimethylphenyl)propyl]-1H-imidazole,
4-[3,3-bis(4-methylphenyl)propyl]-1H -imidazole,
4-[3,3-bis(3-fluorophenyl)propyl]-1H-imidazole,
1-benzyl-5-[3,3-bis(4-chlorophenyl)-3-hydroxypropyl)-1H-imidazole,
1-benzyl-5-[3,3-bis(4-chlorophenyl)propen-2-yl]-1H-imidazole,
4-[3-(4-chlorophenyl)-3-hydroxy-3-phenylpropyl]-1H-imidazole,
4-[3,3-bis(3-methylphenyl)-3-hydroxypropyl]-1H-imidazole,
4-[3,3-bis(3-fluorophenyl)propen-2-yl]-1H-imidazole,
1-benzyl-5-[5-(2,6-dimethylphenyl)-3-hydroxy-3-(2,6-dimethylphenylethyl)-pentyl]-1H-imidazole, 1-benzyl-5-[3,3-bis(3,5-dimethylphenyl)-3-hydroxypropyl]-1H-imidazole,
1-benzyl-5-[3,3-bis(3,5-dimethylphenyl)propen-2-yl]-1H-imidazole,
1-benzyl-5-[3,3-bis(2-methoxyphenyl)propen-2-yl]-1H-imidazole,
1-benzyl-5-[3,3-bis(4-methoxyphenyl)propen-2-yl]-1H-imidazole,
1-benzyl-5-[3,3-bis(2,3-dimethylphenyl)propen-2-yl]-1H-imidazole,
1-benzyl-5-[3,3-bis(2-methylphenyl)propen-2-yl]-1H-imidazole,
1-benzyl-5-[3,3-bis(3-methylphenyl)propen-2-yl]-1H-imidazole,
4-[3,3-bis(2-methoxyphenyl)propyl]-1H-imidazole,
4-[3,3-bis(4-methoxyphenyl)propyl]-1H-imidazole,
1-benzyl-5-[3,3-bis(4-methylphenyl)propen-2-yl]-1H-imidazole,
1-benzyl-5-(3,3-diphenylpropen-2-yl)-1H-imidazole,
1-benzyl-5-(3,5-diphenylpentyl)-1H-imidazole,
4-[3,3-bis(4-methoxyphenyl)propyl]-1H-imidazole,
4-(3,4-diphenylbutyl)-1H-imidazole,
4-[3-(4-methylphenyl)-3-phenylpropyl]-1H-imidazole,
4-[3-(4-fluorophenyl)-3-phenylpropyl]-1H-imidazole,
4-[3,3-bis(4-fluorophenyl)propyl]-1H-imidazole or
1-benzyl-5-(3,3-diphenylpropen-1-yl)-1H-imidazole
or a non-toxic pharmaceutically acceptable acid addition salt thereof.

15. A method of inhibiting aromatase comprising administering to a patient in whom said inhibition is desired an effective amount of a compound according to claim 1.

16. A pharmaceutical composition for inhibiting aromatase comprising a substituted imidazole as claimed in claim 1 in an amount sufficient to produce the desired amount of inhibition and a pharmaceutically acceptable carrier.

17. A method of inhibiting aromatase comprising administering to a patient in whom said inhibition is desired an effective amount of a composition according to claim 16.

* * * * *